(12) United States Patent
Campitelli

(10) Patent No.: US 12,741,108 B2
(45) Date of Patent: Sep. 22, 2026

(54) INHALER ARTICLE WITH FOLDED DISTAL END

(71) Applicant: PHILIP MORRIS PRODUCTS S.A., Neuchâtel (CH)

(72) Inventor: Gennaro Campitelli, Neuchâtel (CH)

(73) Assignee: Philip Morris Products S.A., Neuchâtel (CH)

( * ) Notice: Subject to any disclaimer, the term of this patent is extended or adjusted under 35 U.S.C. 154(b) by 1043 days.

(21) Appl. No.: 17/770,730

(22) PCT Filed: Oct. 23, 2020

(86) PCT No.: PCT/IB2020/059990
§ 371 (c)(1),
(2) Date: Apr. 21, 2022

(87) PCT Pub. No.: WO2021/079341
PCT Pub. Date: Apr. 29, 2021

(65) Prior Publication Data

US 2022/0387737 A1 Dec. 8, 2022

(30) Foreign Application Priority Data

Oct. 25, 2019 (EP) .................................... 19205453

(51) Int. Cl.
*A61M 15/00* (2006.01)
*A24F 42/20* (2020.01)
(Continued)

(52) U.S. Cl.
CPC ......... *A61M 15/0021* (2014.02); *A24F 42/20* (2020.01); *A24F 42/60* (2020.01);
(Continued)

(58) Field of Classification Search
CPC ............ A61M 15/003; A61M 15/0035; A61M 15/0031; A61M 15/0028
See application file for complete search history.

(56) References Cited

U.S. PATENT DOCUMENTS 2,151,418 A * 3/1939 Bolte ................ A61M 15/0028 604/232

FOREIGN PATENT DOCUMENTS

JP 7514401 B2 * 7/2024 ............. A24D 1/027
WO WO-2015092071 A1 * 6/2015 ............... A24D 1/02
(Continued)

OTHER PUBLICATIONS

Machine translation of JP-7514401-B2 (Year: 2025).*
(Continued)

*Primary Examiner* — Kendra D Carter
*Assistant Examiner* — Graciela Natalia Lebron De Jesus
(74) *Attorney, Agent, or Firm* — Mueting Raasch Group

(57) ABSTRACT

An inhaler article (150) includes a body extending along a longitudinal axis from a mouthpiece end (154) to a distal end (156), a capsule cavity (155) defined within the body and a capsule disposed within the capsule cavity. The capsule cavity is bounded downstream by a filter element and bounded upstream and distally by a deformable element (158) the deformable element deforms to expose an open distal end and allow the inhaler article to receive swirling or rotational inhalation airflow during consumption.

5 Claims, 3 Drawing Sheets

(51) Int. Cl.

| | |
|---|---|
| ***A24F 42/60*** | (2020.01) |
| ***A61M 11/00*** | (2006.01) |
| ***A61M 15/02*** | (2006.01) |
| ***A61M 15/06*** | (2006.01) |

(52) U.S. Cl.

CPC ...... *A61M 15/0035* (2014.02); *A61M 15/004* (2014.02); *A61M 15/02* (2013.01); *A61M 15/06* (2013.01); *A61M 2202/064* (2013.01)

(56) References Cited

FOREIGN PATENT DOCUMENTS

| | | | |
|---|---|---|---|
| WO | 20150193498 | 12/2015 | |
| WO | 20180007886 | 1/2018 | |
| WO | WO 2018/100462 A1 | 6/2018 | |
| WO | WO-2018100461 A1 * | 6/2018 | ............... A24D 3/17 |
| WO | 21090082057 | 5/2019 | |
| WO | WO 2019/082056 A1 | 5/2019 | |
| WO | WO 2019/082057 A1 | 5/2019 | |
| WO | 20190123297 | 6/2019 | |
| WO | WO-2019123297 A1 * | 6/2019 | ............... A24C 5/54 |
| WO | 20190186337 | 10/2019 | |
| WO | WO 2019/186372 A1 | 10/2019 | |
| WO | WO 2019/186395 A1 | 10/2019 | |
| WO | WO-2024180456 A1 * | 9/2024 | ............... A24D 1/20 |

OTHER PUBLICATIONS

U.S. Pat. No. 2,151,418_A1 PDF Document (Year: 2025).*

Decision for Grant for JP 2022-524037 issued by the Japanese Patent Office on Mar. 25, 2024, 4 pgs. including English translation.

European Search Report for EP 19205453.4 issued by the European Patent Office, Apr. 23, 2020; 7 pgs.

International Search Report and Written Opinion for PCT/IB2020/059990 issued by the European Patent Office, Feb. 11, 2021; 14 pgs.

International Preliminary Report on Patentability for PCT/IB2020/059990 issued by the European Patent Office, Dec. 7, 2021; 12 pgs.

* cited by examiner

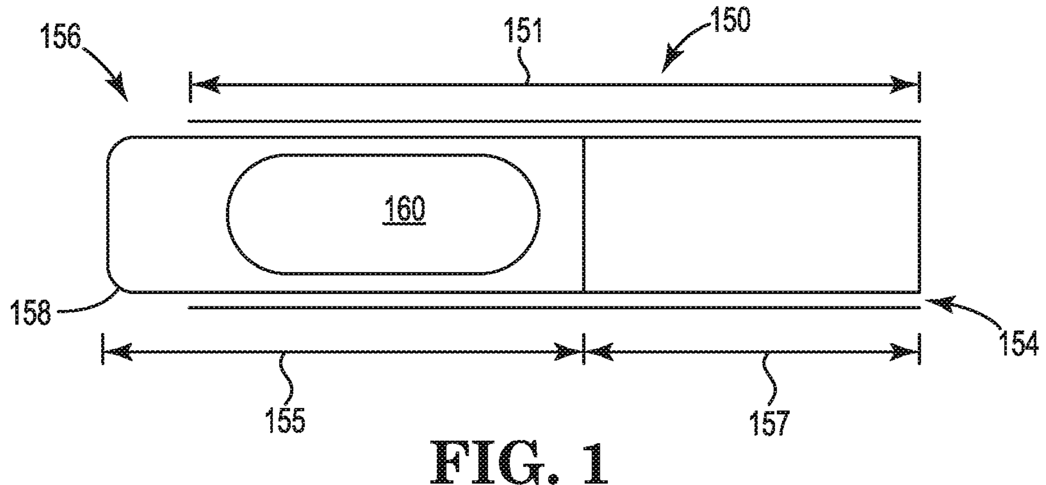
FIG. 1
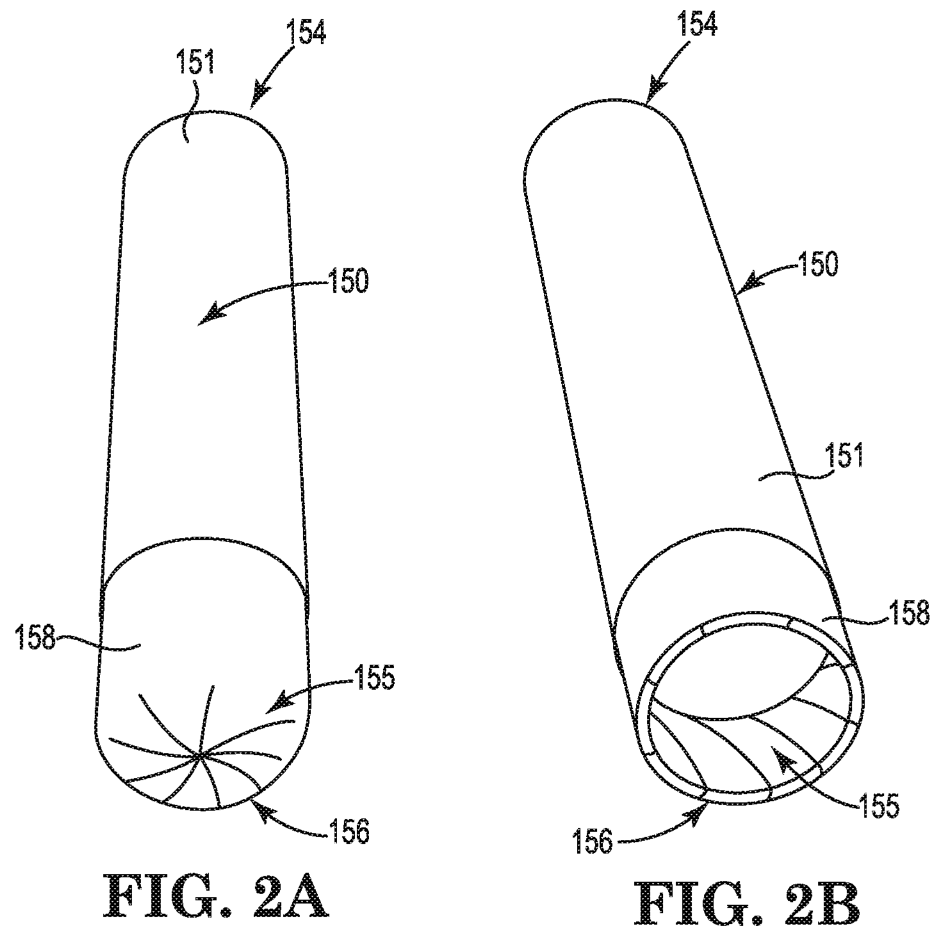
FIG. 2A
FIG. 2B

INHALER ARTICLE WITH FOLDED DISTAL END

This application is the § 371 U.S. National Stage of International Application No. PCT/IB2020/059990, filed 23 Oct. 2020, which claims the benefit of European Application No. 19205453.4, filed 25 Oct. 2019, the disclosures of which are incorporated herein by reference.

This disclosure relates to an inhaler article, and an inhaler system that includes a holder and an inhaler article. The inhaler article includes a wrapped or folded distal end that is deformable to receive inhalation airflow into the inhalation article during consumption.

Dry powder inhalers are not always fully suitable to provide dry powder particles to the lungs at inhalation or air flow rates that are within conventional smoking regime inhalation or air flow rates. Dry powder inhalers may be complex to operate or may involve moving parts. Dry powder inhalers often strive to provide an entire dry powder dose or capsule load in a single breath.

It would be desirable to provide an inhaler article that minimizes complex parts and provide for high speed assembly of the inhaler article. It would be desirable to provide an inhaler article that includes a hygienic barrier that is deformable to expose the inhalation air inlet at the distal end of the inhaler article.

It would be desirable to provide an inhaler system that efficiently depletes a capsule of particles during consumption. It would be desirable to provide an inhaler article that receives swirling inhalation airflow into an inhaler article. It would be desirable to provide an inhaler article that is substantially biodegradable. It would be desirable to provide an inhaler article that is formed of materials utilized in conventional cigarette or smoking article manufacture.

It would be desirable to provide a holder that may activate and retain the inhaler article and transmit swirling or rotational inhalation airflow to the inhaler article during consumption. It would be desirable to provide an inhaler system that includes a low-profile and reusable holder for an inhaler article that can activate the inhaler article. It would be desirable to provide a nicotine powder inhaler system that provides nicotine particles to the lungs at inhalation or air flow rates that are within conventional smoking regime inhalation or air flow rates. It would also be desirable to deliver the nicotine powder with an inhaler article that has a form similar to a conventional cigarette.

This disclosure is directed to an inhaler article. The inhaler article is configured to receive swirling or rotational inhalation airflow during consumption upon breaching a deformable element bounding an upstream end of the capsule cavity. The inhaler article may receive the swirling or rotational inhalation airflow from a holder configured to induce swirling inhalation airflow to an inhaler article during consumption. The holder and an inhaler article may form an inhaler system to which this disclosure is also directed.

According to an aspect of the present invention, a body extending along a longitudinal axis from a mouthpiece end to a distal end, a capsule cavity defined within the body and a capsule disposed within the capsule cavity. The capsule cavity is bounded downstream by a filter element and bounded upstream by a deformable element. The deformable element is deformable between a closed configuration and an open configuration. In the closed configuration, the deformable element defines a closed boundary bounding the capsule cavity. In the open configuration, the deformable element defines an opening through which air can flow into the capsule cavity.

According to an aspect of the present invention, an inhaler article includes a body extending along a longitudinal axis from a mouthpiece end to a distal end, a capsule cavity defined within the body and a capsule disposed within the capsule cavity. The capsule cavity is bounded downstream by a filter element and bounded upstream and distally by a deformable element the deformable element deforms to expose an open distal end and allow the inhaler article to receive swirling or rotational inhalation airflow during consumption.

Advantageously, an inhaler article that has a deformable element that defines a hygienic barrier at the upstream end of the capsule cavity.

The deformable element may be configured to deform and expose the capsule cavity. The upstream boundary of the capsule cavity may be defined by the deformable element forming a closed end of the inhaler article. The upstream boundary of the capsule cavity may be defined by the deformable element forming an open end of the inhaler article.

The deformable element may be folded at its distal end or the distal end of the body of the inhaler article. Preferably the deformable element may be folded in a fan fold at its distal end or the distal end of the body of the inhaler article. Folded sections of the deformable element may fold back onto itself to define an open aperture to receive swirling or rotating inhalation airflow.

Advantageously, the deformable element deforms to expose an open distal end. This allows the inhaler article to receive swirling or rotational inhalation airflow during consumption, reduce complexity of the inhaler article and to be assembled at high speed.

The deformable element may be arranged to interface with a holder such that the deformable element is deformed from the closed configuration to the open configuration upon insertion into the holder. The term "deform" should be understood to mean that the shape of the deformable element is changeable. The deformation of the deformable element may include elastic deformation, where the deformable element reverts back to the closed configuration in the absence of a force being applied to it. Alternately, the deformation of the deformable element may include plastic deformation where the deformable element is held in the open configuration after the application of a force.

At least a portion of the deformable element may be formed of a foldable material. In another example, the deformable element may comprise a hinged element, or a plurality of hinged elements, that move about a pivot in order for the deformable element to move between the open and closed configurations. The deformable element may comprise a fan fold. At least a portion of the deformable element may be formed of cellulosic material. At least a portion of the deformable element may be formed of paper.

Advantageously, the forming the deformable element of a foldable material allows the deformable element to be breached or opened reliably. A foldable material may also improve the assembly of the capsule cavity and provide for high speed assembly of the inhaler article. Advantageously, the deformable element formed of cellulose material or paper is substantially biodegradable and may reduce the environmental impact of the inhaler article.

The deformable element may define at least a portion of a longitudinal sidewall of the capsule cavity. The deformable element may define a majority of the capsule cavity. The deformable element may define the upstream boundary and the sidewalls of the capsule cavity.

Advantageously, the deformable element may provide a protective cover or hygiene barrier for the retained capsule and inhaler article prior to consumption of the inhaler article.

A wrapping layer may circumscribe the filter element and the deformable element. A wrapping layer may join the filter element, capsule cavity, and the deformable element in serial axial abutment. The deformable element may extend beyond the wrapping layer. The deformable element may extend beyond the wrapping layer in a range from about 0.5 mm to about 5 mm, or from about 1 mm to about 4 mm, or about 2 mm to about 3 mm. The wrapping layer may be formed of a cellulose material or paper.

Advantageously, a wrapping layer formed of cellulose material is substantially biodegradable and may reduce the environmental impact of the inhaler article. Joining inhaler article elements with a wrapping layer provides for high speed assembly of the inhaler article.

The capsule cavity and deformable element have substantially equal inner diameters in a range from about 6 mm to about 8 mm.

The capsule may contain pharmaceutically active particles. For instance, the pharmaceutically active particles may comprise nicotine. The pharmaceutically active particles may have a mass median aerodynamic diameter of about 5 micrometres or less, or in a range from about 0.5 micrometres to about 4 micrometres, or in a range from about 1 micrometres to about 3 micrometres.

According to another aspect of the invention, an inhaler system includes the inhaler article described herein, and a holder for the inhaler article, the holder is configured to provide swirling or rotational inhalation airflow to the inhaler article.

Advantageously, the deformable element may cooperate with the features of the holder to securely retain the inhaler article within the holder. For instance, the deformable element may be biased towards the longitudinal axis of the inhaler article in the open configuration so that the inhaler article grips onto the holder, thus holding the inhaler article in place in the holder.

Advantageously, incorporating a swirl generating element into a reusable holder may simplify the construction of the inhaler article and reduce the complexity of the inhaler system. Inhaler articles that receive swirling inhalation airflow may be easier to manufacture and have a simpler construction than inhaler articles that have to induce swirling inhalation airflow. Less complex inhaler articles may also present less environmental burden.

The holder may include a sleeve configured to retain the inhaler article within the housing cavity. The sleeve includes a sleeve cavity and may be being movable within the housing cavity along the longitudinal axis of the housing. The sleeve includes a first open end and a second opposing end. The second opposing end of the sleeve may be configured to allow air to enter the sleeve cavity. The second opposing end of the sleeve may include a sleeve tubular element extending into the sleeve cavity. The sleeve tubular element is configured to extend through the deformable element of the inhaler article and secure the inhaler article within the sleeve.

The sleeve tubular element may form the upstream boundary of the capsule cavity.

The holder may further include a piercing element fixed to and extending from a housing inner surface. The piercing element may be configured to extend through the second opposing end of the sleeve and into the sleeve cavity along a longitudinal axis of the housing and activate the capsule.

The second opposing end of the sleeve may be configured to induce a swirl or rotational airflow on inhalation air flow entering the capsule cavity.

Advantageously, utilizing a reusable holder to generate rotational or swirling airflow may improve the uniform generation of the rotational or swirling airflow as it provided to a plurality of inhaler articles. This rotational or swirling airflow may be provided to a capsule cavity of an inhaler article received within the sleeve of the holder. The rotational or swirling airflow induces a capsule contained within the capsule cavity to rotate and release particles into the rotational or swirling airflow to the consumer.

Advantageously, providing features on the second opposing end of the sleeve that mate with a received inhaler article may improve the reliable airflow connection from the swirl inducing sleeve to the inhaler article received in the sleeve. The deformable element may improve an interference fit to provide a secure engagement of the inhaler article received in the sleeve so that the inhaler article will not fall out of the sleeve or associated holder.

Advantageously, a reusable holder that induces rotational or swirling airflow reduces the complexity of the associated consumable inhaler article. This may reduce the overall cost of manufacture of these inhaler systems and may improve the reliability or efficiency of capsule particle depletion.

Advantageously, the inhaler system provides an inhaler system that minimizes moving parts. Advantageously, the inhaler system utilizes a separate holder that induces rotational or swirling airflow to the inhaler article received within the holder. This may enable the holder to be reusable and the inhaler article to be disposable after a single use. Advantageously, the inhaler system efficiently provides nicotine particles to the lungs at inhalation or air flow rates that are within conventional smoking regime inhalation or air flow rates. The inhaler delivers the nicotine powder with an inhaler article that has a form similar to a conventional cigarette. The inhaler system described herein may provide a dry powder to the lungs at inhalation or air flow rates that are within conventional smoking regime inhalation or air flow rates. A consumer may take a plurality of inhalations or "puffs" where each "puff" delivers a fractional amount of dry powder contained within a capsule contained within the capsule cavity. This inhaler article may have a form similar to a conventional cigarette and may mimic conventional smoking. This inhaler article may be simple to manufacture and convenient to use by a consumer.

Air flow management through a capsule cavity of the inhaler article may cause a capsule contained therein to rotate during inhalation and consumption. The capsule may contain particles containing nicotine (also referred to as "nicotine powder" or "nicotine particles") and optionally particles comprising flavour (also referred to as "flavour particles"). Rotation of the pierced capsule may suspend and aerosolize the nicotine particles released from the pierced capsule into the inhalation air moving through the inhaler article. The flavour particles may be larger than the nicotine particles and may assist in transporting the nicotine particles into the lungs of the user while the flavour particles preferentially remain in the mouth or buccal cavity of the user. The nicotine particles and optional flavor particles may be delivered with the inhaler article at inhalation or air flow rates that are within conventional smoking regime inhalation or air flow rates.

The term "nicotine" refers to nicotine and nicotine derivatives such as free-base nicotine, nicotine salts and the like.

The term "flavourant" or "flavour" refers to organoleptic compounds, compositions, or materials that alter and are intended to alter the taste or aroma characteristics of nicotine during consumption or inhalation thereof.

The terms "upstream" and "downstream" refer to relative positions of elements of the holder, inhaler article and inhaler systems described in relation to the direction of inhalation air flow as it is drawn through the body of the holder, inhaler article and inhaler systems.

The terms "proximal" and "distal" are used to describe the relative positions of components, or portions of components, of the holder, inhaler article, or system. Holders or elements (such as the sleeve) forming the holder, according to the invention have a proximal end which, in use, receives an inhaler article and an opposing distal end which may be a closed end, or have an end closer to the proximal end of the holder. Inhaler articles, according to the invention have a proximal end. In use, the nicotine particles exit the proximal end of the inhaler article for delivery to a user. The inhaler article has a distal end opposing the proximal end. The proximal end of the inhaler article may also be referred to as the mouth end.

The inhaler article may be combined with holder to form an inhaler system. The holder is configured to provide swirling or rotational inhalation airflow to the inhaler article. The holder may also activate the inhaler article by piercing the capsule, thereby providing reliable activation of the capsule (by puncturing the capsule with the piercing element of the holder) within inhaler article, and releasing the particles contained inside the capsule and enabling the article to deliver the particles to a consumer. The holder is separate from the inhaler article, but the consumer may utilize both the inhaler article and the holder while consuming the particles released within the inhaler article. A plurality of these inhaler articles may be combined with a holder to form a system or kit. A single holder may be utilized on 10 or more, or 25 or more, or 50 or more, or 100 or more, inhaler articles to activate (puncture or pierce) a capsule contained within each inhaler article and provide reliable activation and optionally, a visual indication (marking), for each inhaler article of the activation of the inhaler article.

This disclosure is directed to an inhaler article. The inhaler article is configured to receive swirling or rotational inhalation airflow during consumption. The inhaler article may receive the swirling or rotational inhalation airflow from a holder configured to induce swirling inhalation airflow to an inhaler article during consumption. The holder and an inhaler article may form an inhaler system to which this disclosure is also directed.

The holder may be configured to breach or open the deformable element defining the upstream boundary of the inhaler article capsule cavity. Once the deformable element is opened or breached, swirling or rotational inhalation airflow may flow into the capsule cavity though the void space formed by the breached or opened deformable element.

An inhaler article includes a body extending along a longitudinal axis from a mouthpiece end to a distal end, a capsule cavity defined within the body and a capsule disposed within the capsule cavity. The capsule cavity is bounded downstream by a filter element and bounded upstream or distally by a deformable element. The deformable element defining a closed boundary bounding the capsule cavity.

The inhaler article receives swirling or rotational inhalation airflow once the deformable element is breached or opened at the distal end of the inhaler article. The swirling or rotational inhalation airflow traverses the inhaler article from the distal end to the capsule cavity to the filter and out the mouthpiece end of the inhaler article. Inhalation air flow preferably flows coincident with the longitudinal axis of the inhaler article as it flows into the capsule cavity.

The inhaler article is configured to receive swirling inhalation airflow directly into the capsule cavity once the deformable element is breached or opened at the distal end of the inhaler article. The swirling inhalation airflow continues downstream through the capsule cavity and induces rotation of a capsule received, or located, in the capsule cavity. An activated capsule releases a dose of particles into the swirling inhalation airflow downstream through the mouthpiece to the consumer. Thus, the swirling inhalation airflow is created upstream from the inhaler article and swirling inhalation airflow enters the distal end or upstream-most end of the inhaler article and transmits into the capsule cavity to rotate or spin a capsule located within the capsule cavity.

The inhaler body may resemble a smoking article or cigarette in size and shape. The inhaler body may have an elongated body extending along the longitudinal axis of the inhaler article. The inhaler body may have a substantially uniform outer diameter along the length of the elongated body. The inhaler body may have a circular cross-section that may be uniform along the length of the elongated body. The inhaler body may have an outer diameter in a range from about 6 mm to about 10 mm, or from about 7 mm to about 10 mm, or about 7 mm to about 9 mm, or about 7 mm to about 8 mm or about 7.2 mm. The inhaler body may have a length (along the longitudinal axis) in a range from about 40 mm to about 80 mm, or from about 40 mm to about 70 mm, or about 40 mm to about 50 mm, or about 48 mm.

The filter element located downstream of the capsule cavity may extend from the capsule cavity to the mouthpiece end of the inhaler article. The filter element may have a length in a range from about 10 mm to about 30 mm, preferably from about 15 mm to about 25 mm and more preferably from about 20 mm to about 22 mm.

The deformable element is configured to deform and expose the capsule cavity. The deformable element is configured to be breached or opened to expose the capsule cavity. The deformable element is configured to expose substantially the entire open diameter of the capsule cavity. The deformable element is configured to expose the entire open diameter of the capsule cavity.

The deformable element may define at least a portion of a longitudinal sidewall of the capsule cavity. The deformable element may define a majority of the capsule cavity. The deformable element may define a closed distal end or upstream end of the capsule cavity.

The deformable element may be formed of cellulosic material. At least a portion of the deformable element may be formed of paper. The deformable element may provide a barrier to reduce or prevent contaminants or foreign material from entering the capsule cavity.

The capsule cavity sidewall extends parallel with the longitudinal axis of the inhaler article. The deformable element may define a closed distal end or upstream end of the capsule cavity and at least a portion of the capsule cavity sidewall.

The deformable element may define a tubular element having a closed upstream end. The deformable element may define a closed distal end or upstream end of the capsule cavity and at least 50% of the capsule cavity sidewall. The deformable element may define a closed distal end or upstream end of the capsule cavity and at least 75% of the capsule cavity sidewall. The deformable element may define a closed distal end or upstream end of the capsule cavity and the entire capsule cavity sidewall. The deformable element may define the entire capsule cavity except for the downstream boundary surface defined by the filter element. The deformable element may be a paper layer extending from the filter element to the closed upstream end.

The deformable element has an outer surface or diameter that contacts a body or forms a distal end of the inhaler article. Inhalation air flows through the center of the deformable element directly into the capsule cavity once the deformable element is breached or opened. The deformable element may have a diameter that is substantially equal to the inner diameter of the capsule cavity.

The deformable element may have an outer diameter in a range from about 6 mm to about 8 mm or from about 7.0 mm to about 7.2 mm. The deformable element may have an inner diameter in a range from about 6 mm to about 7.2 mm or from about 6.5 mm to about 6.7 mm.

The deformable element may be formed of paper. The deformable element may be formed of one or more paper layers. The deformable element may be formed of paper having a weight in a range of about 50 grams per square meter to about 150 grams per square meter, or from about 75 grams per square meter to about 125 grams per square meter, or from about 90 grams per square meter to about 110 grams per square meter.

The deformable element may have a thickness in a range from about 50 micrometres to about 200 micrometres, or from about 100 micrometres to about 150 micrometres, or from about 110 micrometres to about 130 micrometres.

Once breached or opened, the deformable element may define an opening having an open diameter that is at least about 80% or at least about 90% of the diameter of the capsule cavity.

The deformable element may be easily breached to allow inhalation air to enter the capsule cavity. For instance, the deformable element may be configured to breach upon manual insertion of the inhaler article into a holder by a user without the use of additional tools for assisting the application of force by a user. The deformable element may breach or open to expose substantially the entire upstream end of the capsule cavity. The deformable element may provide a protective cover or hygiene barrier for the retained capsule and inhaler article prior to consumption of the inhaler article.

A wrapping layer may define the body of the inhaler article. The wrapping layer may circumscribe the filter element and the deformable element. The wrapping layer may join the filter element and the deformable element. The wrapping layer may join the filter element, and deformable element in serial axial abutment. The wrapping layer may be formed of a cellulose material.

The deformable element may extend beyond the wrapping layer. The deformable element may extend beyond the wrapping layer in a range from about 0.5 mm to about 5 mm, or from about 1 mm to about 4 mm, or about 2 mm to about 3 mm.

The capsule cavity may define a cylindrical space configured to contain a capsule. For example, the capsule may have an obround shape or a circular cross-section. The capsule cavity may have a substantially uniform or uniform diameter along the length of the capsule cavity. The capsule cavity may have a fixed cavity length. The capsule cavity has a cavity inner diameter, orthogonal to the longitudinal axis, and the capsule has a capsule outer diameter. The capsule cavity may be sized to contain an obround capsule. The capsule cavity may have a substantially cylindrical or cylindrical cross-section along the length of the capsule cavity. The capsule cavity may have a uniform inner diameter. The capsule may have an outer diameter that is about 80% to about 95% of the inner diameter of the capsule cavity. The configuration of the capsule cavity relative to the capsule may promote limited movement of the capsule during activation or piercing of the capsule.

The capsule cavity may be defined by the deformable element having a diameter in a range from about 6 mm to about 7 mm or about 6.6 mm.

The capsule cavity may be defined by an inhaler article tubular element. The tubular element may be joined between and in abutting alignment with the tubular element forming the distal end of the inhaler article and the filter element. These elements may be joined with a wrapper. The open tubular element defining the capsule cavity may be formed of a biodegradable material, such as cardboard or paperboard.

The configuration of the capsule cavity relative to the capsule may promote the capsule to rotate with stability within the capsule cavity. The longitudinal axis of the capsule may rotate with stability co-axially with the longitudinal axis of the inhaler body during inhalation. The configuration of the capsule cavity relative to the capsule may promote the capsule to rotate with some shaking within the capsule cavity Stable rotation refers to the longitudinal axis of the inhaler body being substantially parallel or co-axial with the axis of rotation of the capsule. Stable rotation may refer to the absence of procession of the rotating capsule. Preferably, the longitudinal axis of the inhaler body may be substantially coextensive with the axis of rotation of the capsule. Stable rotation of the capsule may provide a uniform entrainment of a portion of nicotine particles from the capsule over two or more, or five or more, or ten or more "puffs" or inhalations by a consumer.

The capsule may be sealed within the inhaler article prior to consumption. The inhaler article may be contained within a sealed or airtight container or bag. The inhaler article may include the deformable element (closing the distal end of the inhaler article) and one or more peelable or removable seal layers to the air outlet or mouthpiece of the inhaler article.

The capsule may rotate about its longitudinal or central axis when air flows through the inhaler article. The capsule may be formed of an airtight material that may be pierced or punctured by a piercing element that may be separate or combined with the inhaler. The capsule may be formed of a metallic or polymeric material that serves to keep contaminates out of the capsule but may be pierced or punctured by a piercing element prior to consumption of the nicotine particles within the capsule. The capsule may be formed of a polymer material. The polymer material may be hydroxypropylmethylcellulose (HPMC). The capsule may be a size 1 to size 4 capsule, or a size 3 capsule.

The capsule may contain pharmaceutically active particles. For instance, the pharmaceutically active particles may comprise nicotine. The pharmaceutically active particles may have a mass median aerodynamic diameter of about 5 micrometres or less, or in a range from about 0.5 micrometres to about 4 micrometres, or in a range from about 1 micrometres to about 3 micrometres.

The capsule may contain nicotine particles comprising nicotine (also referred to as "nicotine powder" or "nicotine particles") and optionally particles comprising flavour (also referred to as "flavour particles"). The capsule may contain a predetermined amount of nicotine particles and optional flavour particles. The capsule may contain enough nicotine particles to provide at least 2 inhalations or "puffs", or at least about 5 inhalations or "puffs", or at least about 10 inhalations or "puffs". The capsule may contain enough nicotine particles to provide from about 5 to about 50 inhalations or "puffs", or from about 10 to about 30 inhalations or "puffs". Each inhalation or "puff" may deliver from about 0.1 mg to about 3 mg of nicotine particles to the lungs of the user or from about 0.2 mg to about 2 mg of nicotine particles to the lungs of the user or about 1 mg of nicotine particles to the lungs of the user.

The nicotine particles may have any useful concentration of nicotine based on the particular formulation employed. The nicotine particles may have at least about 1% wt nicotine up to about 30% wt nicotine, or from about 2% wt to about 25% wt nicotine, or from about 3% wt to about 20% wt nicotine, or from about 4% wt to about 15% wt nicotine, or from about 5% wt to about 13% wt nicotine. Preferably, about 50 to about 150 micrograms of nicotine may be delivered to the lungs of the user with each inhalation or "puff".

The capsule may hold or contain at least about 5 mg of nicotine particles or at least about 10 mg of nicotine particles. The capsule may hold or contain less than about 900 mg of nicotine particles, or less than about 300 mg of nicotine particles, or less than 150 mg of nicotine particles. The capsule may hold or contain from about 5 mg to about 300 mg of nicotine particles or from about 10 mg to about 200 mg of nicotine particles.

When flavour particles are blended or combined with the nicotine particles within the capsule, the flavour particles may be present in an amount that provides the desired flavour to each inhalation or "puff" delivered to the user.

The nicotine particles may have any useful size distribution for inhalation delivery preferentially into the lungs of a user. The capsule may include particles other than the nicotine particles. The nicotine particles and the other particles may form a powder system.

The capsule may hold or contain at least about 5 mg of a dry powder (also referred to as a powder system) or at least about 10 mg of a dry powder. The capsule may hold or contain less than about 900 mg of a dry powder, or less than about 300 mg of a dry powder, or less than about 150 mg of a dry powder. The capsule may hold or contain from about 5 mg to about 300 mg of a dry powder, or from about 10 mg to about 200 mg of a dry powder, or from about 25 mg to about 100 mg of a dry powder.

The dry powder or powder system may have at least about 40%, or at least about 60%, or at least about 80%, by weight of the powder system comprised in nicotine particles having a particle size of about 5 micrometres or less, or in a range from about 1 micrometre to about 5 micrometres.

The particles comprising nicotine may have a mass median aerodynamic diameter of about 5 micrometres or less, or in a range from about 0.5 micrometres to about 4 micrometres, or in a range from about 1 micrometres to about 3 micrometres or in a range from about 1.5 micrometres to about 2.5 micrometres. The mass median aerodynamic diameter is preferably measured with a cascade impactor.

The particles comprising flavour may have a mass median aerodynamic diameter of about 20 micrometres or greater, or about 50 micrometres or greater, or in a range from about 50 to about 200 micrometres, or from about 50 to about 150 micrometres. The mass median aerodynamic diameter is preferably measured with a cascade impactor.

The dry powder may have a mean diameter of about 60 micrometres or less, or in a range from about 1 micrometres to about 40 micrometres, or in a range from about 1.5 micrometres to about 25 micrometres. The mean diameter refers to the mean diameter per mass and is preferably measured by laser diffraction, laser diffusion or an electronic microscope.

Nicotine in the powder system or nicotine particles may be a pharmaceutically acceptable free-base nicotine, or nicotine salt or nicotine salt hydrate. Useful nicotine salts or nicotine salt hydrates include nicotine pyruvate, nicotine citrate, nicotine aspartate, nicotine lactate, nicotine bitartrate, nicotine salicylate, nicotine fumarate, nicotine monopyruvate, nicotine glutamate or nicotine hydrochloride, for example. The compound combining with nicotine to form the salt or salt hydrate may be chosen based on its expected pharmacological effect.

The nicotine particles preferably include an amino acid. Preferably, the amino acid may be leucine such as L-leucine. Providing an amino acid such as L-leucine with the particles comprising nicotine, may reduce adhesion forces of the particles comprising nicotine and may reduce attraction between nicotine particles and thus reduce agglomeration of nicotine particles. Similarly, adhesion forces to particles comprising flavour may also be reduced thus agglomeration of nicotine particles with flavour particles is also reduced. The powder system described herein thus may be a free-flowing material and possess a stable relative particle size of each powder component even when the nicotine particles and the flavour particles are combined.

Preferably, the nicotine may be a surface modified nicotine salt where the nicotine salt particle comprises a coated or composite particle. A preferred coating or composite material may be L-leucine. One particularly useful nicotine particle may be nicotine bitartrate with L-leucine.

The powder system may include a population of flavour particles. The flavour particles may have any useful size distribution for inhalation delivery selectively into the mouth or buccal cavity of a user.

The powder system may have at least about 40%, or at least about 60%, or at least about 80%, by weight of the population of flavour particles of the powder system comprised in particles having a particle size of about 20 micrometres or greater. The powder system may have at least about 40% or at least about 60%, or at least about 80%, by weight of the population of flavour particles of the powder system comprised in particles having a particle size of about 50 micrometres or greater. The powder system may have at least about 40% or at least about 60%, or at least about 80%, by weight of the population of flavour particles of the powder system comprised in particles having a particle size in a range from about 50 micrometre to about 150 micrometres.

The particles comprising flavour may include a compound to reduce adhesion forces or surface energy and resulting agglomeration. The flavour particle may be surface modified with an adhesion reducing compound to form a coated flavour particle. One preferred adhesion reducing compound may be magnesium stearate. Providing an adhesion reducing compound such as magnesium stearate with the flavour particle, especially coating the flavour particle, may reduce adhesion forces of the particles comprising flavour and may reduce attraction between flavour particles and thus reduce agglomeration of flavour particles. Thus, agglomeration of flavour particles with nicotine particles may also be reduced. The powder system described herein thus may possess a stable relative particle size of the particles comprising nicotine and the particles comprising flavour even when the nicotine particles and the flavour particles are combined. The powder system preferably may be free flowing.

Conventional formulations for dry powder inhalation contain carrier particles that serve to increase the fluidization of the active particles since the active particles may be too small to be influenced by simple airflow though the inhaler. The powder system may comprise carrier particles. These carrier particles may be a saccharide such as lactose or mannitol that may have a particle size greater than about 50 micrometres. The carrier particles may be utilized to improve dose uniformity by acting as a diluent or bulking agent in a formulation.

The powder system utilized with the nicotine powder delivery system described herein may be carrier-free or substantially free of a saccharide such as lactose or mannitol. Being carrier-free or substantially free of a saccharide such as lactose or mannitol may allow the nicotine and to be inhaled and delivered to the user's lungs at inhalation or airflow rates that are similar to typical smoking regime inhalation or airflow rates.

The nicotine particles and a flavour may be combined in a single capsule. As described above, the nicotine particles and a flavour may each have reduced adhesion forces that result in a stable particle formulation where the particle size of each component does not substantially change when combined. Alternatively, the powder system includes nicotine particles contained within a single capsule and the flavour particles contained within a second capsule.

The nicotine particles and flavour particles may be combined in any useful relative amount so that the flavour particles are detected by the user when consumed with the nicotine particles. Preferably, the nicotine particles and a flavour particles form at least about 90% wt or at least about 95% wt or at least about 99% wt or 100% wt of the total weight of the powder system.

The inhaler and inhaler system may be less complex and have a simplified airflow path as compared to conventional dry powder inhalers. Advantageously, rotation of the capsule within the inhaler body aerosolizes the nicotine particles or powder system and may assist in maintaining a free-flowing powder. Thus, the inhaler article may not require the elevated inhalation rates typically utilized by conventional inhalers to deliver the nicotine particles described above deep into the lungs.

The inhaler article may use a flow rate of less than about 5 L/min or less than about 3 L/min or less than about 2 L/min or about 1.6 L/min. Preferably, the flow rate may be in a range from about 1 L/min to about 3 L/min or from about 1.5 L/min to about 2.5 L/min. Preferably, the inhalation rate or flow rate may be similar to that of Health Canada smoking regime, that is, about 1.6 L/min.

An inhaler system includes the inhaler article described herein, and a holder for the inhaler article, the holder is configured to provide swirling or rotational inhalation airflow to the inhaler article. The hold may be configured to provide swirling or rotational inhalation airflow to the inhaler article. The holder may be configured to breach or open the deformable element and provide swirling or rotational inhalation airflow to the inhaler article.

The holder may include a sleeve configured to retain the inhaler article within the housing cavity. The sleeve includes a sleeve cavity and may be being movable within the housing cavity along the longitudinal axis of the housing. The sleeve includes a first open end and a second opposing end. The second opposing end of the sleeve may be configured to allow air to enter the sleeve cavity. The second opposing end of the sleeve may include a sleeve tubular element extending into the sleeve cavity. The sleeve tubular element may be configured to extend through the deformable element and into the distal end of the inhaler article and secure the inhaler article within the sleeve. The sleeve tubular element may be configured to extend through the deformable element of the inhaler article and secure the inhaler article within the sleeve.

The holder may further include a piercing element fixed to and extending from a housing inner surface. The piercing element may be configured to extend through the second opposing end of the sleeve and into the sleeve cavity along a longitudinal axis of the housing and activate the capsule.

The second opposing end of the sleeve may be configured to induce a swirl or rotational airflow on inhalation air flow entering the capsule cavity.

A method includes, inserting an inhaler article into the sleeve of the holder for an inhaler article. The inhaler article includes a body, the body extending along an inhaler longitudinal axis from a mouthpiece end to a distal end, a body length, and a capsule disposed within the inhaler article body. Then, moving the inhaler article and sleeve toward the piercing element until the piercing element pierces the capsule. Then drawing air into the second opposing end of the sleeve of the holder to form the swirling inhalation airflow. This swirling inhalation airflow is then transmitted into the inhaler article while the inhaler article is disposed within the holder for an inhaler article. The consumed inhaler article may then be removed from the holder and discarded. Then a fresh inhaler article may be inserted into the holder and the method may be repeated.

The inhaler article is configured to receive swirling inhalation airflow directly into the distal end of the inhaler article, once the deformable element is opened or breached. The swirling inhalation airflow then continues downstream into the capsule cavity and induces rotation of a capsule received in the capsule cavity. The activated capsule then releases a dose of particles into the swirling inhalation airflow downstream through the mouthpiece to the consumer. The distal end or upstream-most end of the inhaler article includes an open aperture that defines an open inhalation air inlet, once the once the deformable element is opened or breached. Thus, the swirling inhalation airflow is created upstream from the inhaler article and swirling inhalation airflow enters the distal end or upstream-most end of the inhaler article.

A holder for an inhaler article includes a housing comprising a housing cavity for receiving an inhaler article and a sleeve configured to retain an inhaler article within the housing cavity. The sleeve comprises a sleeve cavity movable within the housing cavity along the longitudinal axis of the housing. The sleeve comprises a first open end and a second opposing end. The second opposing end of the sleeve is configured to allow air to enter the sleeve cavity. The second opposing end of the sleeve is configured to induce a swirl on the air entering the sleeve cavity.

The second opposing end of the sleeve defines a swirl generating element that is configured to generate swirling or rotational inhalation airflow. This swirling or rotational inhalation airflow may be transmitted into an inhaler article to rotate a capsule and release dry powder contained within the capsule.

The second opposing end of the sleeve includes a sleeve tubular element having a central passage in fluid communication with the sleeve cavity. The second opposing end of the sleeve has at least one air inlet allowing air to enter into the central passage. The at least one air inlet extends in a direction that is tangential to the central passage. The second opposing end of the sleeve may have at least two air inlets allowing air to enter into the central passage. The at least two air inlets extend in a direction that is tangential to the central passage. The second opposing end of the sleeve may have at least three air inlets allowing air to enter into the central passage. The at least three air inlets extend in a direction that is tangential to the central passage. The second opposing end of the sleeve may have four air inlets allowing air to enter into the central passage. The four air inlets extend in a direction that is tangential to the central passage.

The sleeve tubular element may be coaxial with the longitudinal axis of the housing. The sleeve tubular element may be coaxial with the sleeve cavity. The sleeve tubular element may be coaxial with both the longitudinal axis of the housing and the sleeve cavity.

The sleeve tubular element having a central passage may have a diameter in a range from about 30% to about 70% of a diameter of the sleeve cavity. The sleeve tubular element having a central passage may have a diameter in a range from about 40% to about 60% of a diameter of the sleeve cavity.

The sleeve tubular element having a central passage that extends into the sleeve cavity and forms an annular recess with the sleeve cavity configured to receive a distal end of an inhaler article. The sleeve tubular element having a central passage extends into the sleeve cavity and forms an annular recess with the sleeve cavity configured to retain a distal end of an inhaler article, once the deformable element is breached or opened.

The sleeve tubular element having a central passage extends into a distal end of an inhaler article received within the sleeve cavity. Once the sleeve tubular element is received within the distal end of the inhaler article, the open end of the sleeve tubular element may form the upstream boundary of the capsule cavity.

The annular recess may be configured to retain the distal end of an inhaler article with an interference fit.

The deformable element once breached or opened may fold back onto a sidewall of the capsule cavity. The deformable element once breached or opened may assist in providing an interference fit with the sleeve tubular element. The deformable element once breached or opened may cooperate with the sleeve tubular element recess in providing an interference fit with the sleeve tubular element.

The sleeve tubular element having a central passage may breach, penetrate or open the deformable element defining the distal end or upstream end closed boundary of the capsule cavity. Portions of the breached deformable element may be forced onto the inner surface of the capsule cavity. Preferably, the sleeve tubular element having a central passage exposes the entire diameter of the capsule cavity upon inserting through the deformable element.

At least a portion of the sleeve tubular element having a central passage is located upstream from an inhaler article received in the sleeve. The sleeve tubular element having a central passage preferably is coaxial with the longitudinal axis of the received inhaler article.

The sleeve tubular element having a central passage may be sized to mate with an inhaler article capsule cavity. The sleeve tubular element having a central passage may interlock with the inhaler article capsule cavity. The sleeve tubular element having a central passage may fit within the capsule cavity. The sleeve tubular element central passage may have an inner diameter in a range from about 3 mm to about 5 mm, or about 4 mm.

The sleeve tubular element may have an outer diameter sized to mate with inner diameter of the capsule cavity. The sleeve tubular element may have an outer diameter sized to contact the inner diameter of the capsule cavity. The sleeve tubular element may have an outer diameter of about 5 mm to about 7 mm, or about 6 mm to about 7 mm.

The sleeve tubular element having a central passage may include at least one air inlet that extends in a direction that is tangential to the central passage. The sleeve tubular element may include at least two air inlets that extend in a direction tangential to the central passage. The sleeve tubular element may include at least three air inlets that extend in a direction tangential to the central passage.

The one or more air inlets may extend through the sidewall forming the opposing second end of the sleeve. The one or more air inlets may extend in a direction orthogonal to the longitudinal axis of the sleeve or housing. The one or more air inlets may extend in a direction orthogonal to the longitudinal axis of the sleeve tubular element having a central passage.

The sleeve tubular element having a central passage may include one air inlet that extends in a direction that is tangential to the central passage. The sleeve tubular element having a central passage may include two air inlets that extend in a direction tangential to the central passage. The sleeve tubular element having a central passage may include three air inlets that extend in a direction tangential to the central passage. The sleeve tubular element having a central passage may include four air inlets that extend in a direction tangential to the central passage.

Preferably, the at least one air inlet enters the central passage of the sleeve tubular element at the inner diameter of the sleeve tubular element defining the inner diameter or periphery of the central passage. Preferably, the at least two air inlets enter the central passage at the inner diameter of the sleeve tubular element defining the inner diameter or periphery of the central passage. Preferably, the at least three air inlets enter the central passage at the inner diameter of the sleeve tubular element defining the inner diameter or periphery of the central passage. Preferably, the four air inlets enter the central passage at the inner diameter of the sleeve tubular element defining the inner diameter or periphery of the central passage.

The two or more air inlets are preferably equally spaced from get other around the circumference of the central passage of the sleeve tubular element.

The at least one air inlet that extends in a direction tangential to the central passage of the sleeve tubular element enters the central passage proximate to an end surface defining a distal end of the sleeve. The end surface forms a substantially closed end surface allowing only a piercing element to extend through the end surface. The end surface extends orthogonally to the longitudinal axis of the sleeve. The end surface prevents inhalation air from flowing out through the distal end of the sleeve. The end surface directs inhalation air toward the sleeve cavity.

Preferably, the at least one air inlet that extends in a direction that is tangential to the central passage of the sleeve tubular element enters the sleeve tubular element having a central passage at the end surface. Improved capsule depletion occurs when the tangential air inlets are located closer to the end surface of the central passage.

The sleeve tubular element may be a unitary construction with the sleeve (that is, integral to the sleeve) configured to retain an inhaler article within the housing cavity. The sleeve tubular element may form a portion of the second opposing end of the sleeve. The sleeve tubular element and sleeve may be formed with an injection moulding process. The sleeve tubular element and sleeve may be formed simultaneous with an injection moulding process.

The sleeve tubular element having a central passage may extend or protrude into the sleeve cavity. This sleeve tubular element having a central passage may have an outer surface having an outer diameter that faces the inner surface of the sleeve. The inner surface of the sleeve defining the sleeve cavity.

The sleeve tubular element having a central passage may extend into the sleeve cavity a distance in a range from about 2 mm to about 10 mm, or from about 3 mm to about 7 mm or from about 4 mm to about 6 mm, or about 5 mm. In these and other embodiments, the sleeve tubular element having a central passage may have an outer diameter in a range from about 4 to about 6.5 mm or from about 5 mm to about 6 mm, or from about 5 mm to about 5.5 mm, or preferably about 5.25 mm.

At least a portion of the sleeve tubular element having a central passage may be inserted into the received inhaler article. Preferably, at least 50% of the sleeve tubular element having a central passage may be inserted into the received inhaler article.

The sleeve tubular element having a central passage extending into the sleeve cavity may form an annular recess with the sleeve cavity configured to receive a distal end of an inhaler article. The sleeve tubular element having a central passage extending into the sleeve cavity may form an annular protrusion with the sleeve cavity configured to be received by a distal end of an inhaler article. The sleeve tubular element having a central passage extending into the sleeve cavity may form both an annular recess and an annular protrusion within the sleeve cavity configured to receive a distal end of an inhaler article.

The distal end of the inhaler article may be configured to mate with the annular recess formed by the sleeve tubular element having a central passage extending into the sleeve cavity. The distal end of the inhaler article may be configured to mate with the annular protrusion formed by the sleeve tubular element having a central passage extending into the sleeve cavity. The distal end of the inhaler article may be configured to mate with the annular recess and annular protrusion formed by the sleeve tubular element having a central passage extending into the sleeve cavity. The sleeve tubular element having a central passage may be configured to extend into a distal end of an inhaler article received within the sleeve cavity.

The annular protrusion formed by the sleeve tubular element having a central passage extending into the sleeve cavity may fit into or slide into the received inhaler article capsule cavity once the deformable element is breached or opened. The annular protrusion formed by the sleeve tubular element having a central passage extending into the sleeve cavity may fit within an inhaler article capsule cavity once the deformable element is breached or opened. The annular protrusion formed by the sleeve tubular element having a central passage extending into the sleeve cavity may form an interference fit within an inhaler article capsule cavity once the deformable element is breached or opened. Thus, the central passage of the sleeve tubular element having a central passage may fit into the inhaler article capsule cavity once the deformable element is breached or opened.

The holder for an inhaler article may include a piercing element configured to pierce or activate a capsule within an inhaler article. The piercing element may be fixed to and extend from a housing inner surface. The piercing element may be configured to extend through the end surface of the second opposing surface of the sleeve and into the sleeve cavity along a longitudinal axis of the housing.

The piercing element may extend through an aperture in the end surface of the sleeve. The piercing element may extend through a resealable element in the end surface of the sleeve. The resealable element may form an airtight seal or barrier at the end surface of the sleeve when a piercing element is not within the resealable element. The piercing element may extend through an aperture in the end surface of the sleeve and substantially block air flow thought the aperture.

The piercing element may pass through the end surface and puncture the capsule within the capsule cavity. The resealable element, if present in the piercing aperture, may reseal once the piercing element is retracted or removed from the resealable element. Resealable elements or membranes may include a septum or septum-like element. Resealable elements or membranes may be formed of elastic material such as rubber, silicone, metal foil co-laminated with a polymer, or latex and the like, or cellulose acetate tow, such as high-density cellulose acetate tow.

The piercing element may be fixed to and extend from the housing inner surface, into the housing cavity along a piercing element longitudinal axis a piercing element length. The piercing element may be recessed from an open proximal end of the housing by a recessed distance.

The distal end or upstream-most end of the inhaler article may contact the second opposing end of the sleeve and urge the sleeve to travel toward the piercing element. The sleeve may be co-axial with the piercing element. The sleeve may align the inhaler article so that the piercing element reliably activates capsule within the inhaler article. The sleeve or holder may also mechanically hold the piercing element and support the piercing element to prevent or mitigate deflection of the piercing element.

The sleeve may define a first air inlet zone comprising at least one air aperture through the sleeve. The first air inlet zone may include two or more, three or more, four or more, or from about 1 to about 10 air apertures, or from about 3 to about 9 air apertures. The first air inlet zone is proximate to the first open end of the sleeve. The first air inlet zone is configured to allow air to flow to an airflow channel formed between the sleeve and the housing.

The sleeve may comprise a second air inlet zone downstream from the first air inlet zone. The second air inlet zone comprising the second opposing end of the sleeve configured to allow air to enter the sleeve cavity. The second air inlet zone may include one, two or more, three or more, or four or more air apertures the direct inlet or inhalation air into the second opposing end of the sleeve at a tangent to the sleeve tubular element central passage to form swirling inhalation airflow.

The holder may include a retaining ring element fixed to the open proximal end of the housing. The retaining ring element retains the sleeve within the inhaler article cavity. The retaining ring has a thickness sufficient to stop or retain the movement of the sleeve within the inhaler article cavity of the holder.

The holder may include a spring element configured to bias the sleeve between a relaxed (or undeformed) state and compressed (or deformed) state towards the open proximal end of the housing or away from piercing element. The spring element may be contained within the housing cavity of the holder and be compressed as the movable sleeve and inhaler article move toward the piercing element. The spring element may be located between the sleeve and closed end of the housing and contacts the sleeve and closed end of the housing. The spring element may be disposed about the piercing element. The spring element may be co-axial with the piercing element. The spring element may be a conical spring.

The spring element may be fixed to the distal end or closed of the holder. The spring element may be fixed to the second opposing end of the sleeve. The spring element may be fixed to both the closed end of the holder and the second opposing end of the sleeve. The spring element may be a conical spring. The conical spring advantageously may provide a low-profile design so that it may provide a more flexible design and smaller overall compression thickness. The provision of a conical spring may also advantageously reduce the likelihood that the spring will buckle when compressed compared to a cylindrical spring.

The spring element biases the inhaler article off of and away from the piercing element once the piercing element activates the inhaler article. The spring element may be disposed about the piercing element. The spring element may be coaxial with the piercing element. The piercing element may extend beyond the spring element when the spring element is in a relaxed position. The piercing element may extend beyond the spring element when the spring element is in a compressed position. The piercing element may extend beyond the spring element when the spring element is in both the relaxed position and the compressed position. The piercing element may extend beyond the spring element when the sleeve compresses the spring element.

The sleeve may include an elongated slot extending along a longitudinal length of the sleeve. When the sleeve comprises an elongated slot, the housing may further comprise an alignment pin extending from the inner surface of the housing cavity. The alignment pin may be configured to mate with the elongated slot. Advantageously, the elongated slot and alignment pin provides for a reliable movement path between a relaxed and compressed position.

The holder may include a marking element that extends into the inhaler article cavity. The marking element may be configured to mark the surface of an inhaler article. The marking element may extend orthogonally to the holder or inhaler article longitudinal axis. The marking element may be configured to mark the outer surface of an inhaler article in a mechanical manner. For example, the marking element may be configured to scratch, cut, abrade, score, fold, or bend the outer surface of the inhaler article. The marking element may have a sharp end configured to scratch the inhaler outer surface when received within the inhaler article cavity. The marking element may apply a color to the inhaler outer surface when received within the inhaler article cavity. The marking element may mark the inhaler outer surface when the piercing element penetrates a capsule disposed within the inhaler article. Thus, indicating that the inhaler article has been activated and may be consumed by a user. This may also advantageously prevent a user trying to reuse an inhaler article which has already been previously activated.

The marking element may extend orthogonally to the holder or inhaler article longitudinal axis. The marking element may be formed of a rigid material configured to provide a visual indication that the marking element has contacted the inhaler outer surface. The marking element may be fixed to the holder housing. The marking element may form the alignment pin, as described above.

The marking element may extend though at least a portion of a thickness of the holder. The marking element may extend through the sleeve. The marking element may extend into the inhaler article cavity and into the sleeve. The marking element may extend beyond the at least the sleeve a marking distance so that the marking element contacts the inhaler outer surface when the inhaler article is received within the inhaler article cavity. The marking element may be aligned with and mate with the elongated slot of the sleeve.

The piercing element may be recessed from the open proximal end by any suitable recessed distance. For example, the piercing element may be recessed from the open proximal end a recessed distance of at least about 10%, at least about 20%, at least about 25%, or at least about 30%, or at least about 35%, or at least about 40%, of the housing length. The piercing element may be recessed from the open proximal end a recessed distance of in a range from about 5% to about 50%, or from about 10% to about 40%, or from about 15% to about 40%, or about 20% to about 40%, of the housing length.

The piercing element length may be any suitable length relative to the housing length. For example, the piercing element length may be about 25% to about 60%, or about 30% to about 50%, of the housing length. A distal end of the piercing element may be fixed to the distal end adjacent to or at the distal end of the housing. The piercing element entire length may be coextensive within the housing length.

The piercing element is formed of a rigid material. The rigid material is sufficiently rigid to pierce, puncture or activate a capsule contained within the inhaler article. The piercing element may be formed of a metal. The piercing element may be formed of stainless steel, such as 316 stainless steel, for example. The piercing element may be formed of a polymeric material. The piercing element may be formed of a fibre-reinforced polymeric material.

The housing may be formed of any rigid material. The housing may be formed of a polymeric material. Polymeric materials useful for forming the housing include polycarbonate, polypropylene, polyethylene, nylon, acrylonitrile butadiene styrene, styrene acrylonitrile, polyacrylate, polystyrene, PBT polyester, PET polyester, polyoxymethylene, polysulfone, polyethersulfone, polyethereetherketone, or liquid crystal polymer.

The inhaler article may be received into the holder such that the inhaler article outer surface and the holder housing outer surface are concentric. The piercing element longitudinal axis may be coaxial with the housing longitudinal axis, and the inhaler longitudinal axis, when the inhaler article is received within the holder. At least about 50%, or at least about 75% of the housing length may be coextensive with the inhaler length, when the inhaler article is received within the holder.

The holder may be formed by insertion moulding techniques. The piercing element may first be formed by moulding, for example, and then the housing may be moulded around the piercing element bonding to the piercing element. The piercing element may be a metal piercing element, the housing may be moulded around the metal piercing element fixing the metal piercing element to the housing. A metal piercing element may include protrusions or recesses at the distal end of the piercing element to increase surface area of the distal end of the piercing element and improve fixation within the housing moulded material.

The inhaler system may be used by a consumer like smoking a conventional cigarette or vaping an electronic cigarette. Such smoking or vaping may be characterized by two steps: a first step during which a small volume containing the full amount of nicotine desired by the consumer is drawn into the mouth cavity, followed by a second step during which this small volume comprising the aerosol comprising the desired amount of nicotine is further diluted by fresh air and drawn deeper into the lungs. Both steps are controlled by the consumer. During the first inhalation step the consumer may determine the amount of nicotine to be inhaled. During the second step, the consumer may determine the volume for diluting the first volume to be drawn deeper into the lungs, maximizing the concentration of active agent delivered to the airway epithelial surface. This smoking mechanism is sometimes called "puff-inhale-exhale".

All scientific and technical terms used herein have meanings commonly used in the art unless otherwise specified. The definitions provided herein are to facilitate understanding of certain terms used frequently herein.

As used herein, the singular forms "a", "an", and "the" encompass embodiments having plural referents, unless the content clearly dictates otherwise.

As used herein, "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open-ended sense, and generally mean "including, but not limited to". It will be understood that "consisting essentially of", "consisting of", and the like are subsumed in "comprising," and the like.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the disclosure, including the claims.

The invention will now be further described with reference to the figures in which:

FIG. 1 is a cross-sectional schematic diagram of an illustrative inhaler article;

FIG. 2A is a front perspective view of an illustrative inhaler article with an intact deformable element;

FIG. 2B is a front perspective view of an illustrative inhaler article with an opened deformable element;

Figure 3:
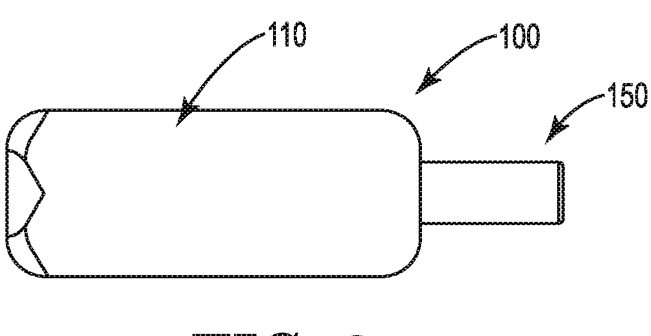
FIG. 3 is a perspective view of an illustrative inhaler system.

The schematic drawings are not necessarily to scale and are presented for purposes of illustration and not limitation. The drawings depict one or more aspects described in this disclosure. However, it will be understood that other aspects not depicted in the drawing fall within the scope and spirit of this disclosure.

FIG. 1 is a cross-sectional schematic diagram of an illustrative inhaler article 150. The inhaler article 150 includes a body 151 extending along a longitudinal axis of the inhaler article from a mouthpiece end 154 to a distal end 156, a capsule cavity 155 and a capsule 160 retained within the capsule cavity 155. The capsule cavity 155 is defined within the body 151 and bounded downstream by a filter element 157 and bounded upstream by deformable element 158. The deformable element defines a closed boundary bounding the capsule cavity 155.

The deformable element 158 defines the capsule cavity. In one embodiment the deformable element 158 is formed of paper having a thickness of about 125 micrometres and a basis weight of about 100 grams per square meter. The illustrated deformable element 158 has a total later length of about 25 mm and extends beyond the body 151 about 3 mm. The illustrated deformable element 158 has an inner diameter of about 6.6 mm. The illustrated inhaler article 150 has a filter element later length of about 20 mm and the wrapper or body has a lateral length of about 42 mm.

In this example, the body 151 is a paper wrapper that joins the deformable element 158, and filter element 157 in serial abutting axial alignment. The total length of the illustrative inhaler article 150 is about 45 mm with an outer uniform diameter of about 7.2 mm.

FIG. 2A is a front perspective view of the illustrative inhaler article 150 with an intact deformable element 158. The intact deformable element 158 forms a folded distal end 156 of the inhaler article 150. The folded distal end 156 may be referred to as a "fan fold". The deformable element 158 is folded back onto itself forming overlapping pie shaped sections sealing or closing the upstream end of the capsule cavity 155.

FIG. 2B is a front perspective view of the illustrative inhaler article with an opened deformable element 158. The folded sections of the deformable element 158 may be breached or opened to expose the capsule cavity 155. The folded sections of the deformable element 158 may fold back onto itself to define an open aperture for receiving swirling or rotating inhalation airflow.

The holder, described below, may be configured to breach or open the deformable element 158 upon being received into the holder.

Figure 4:
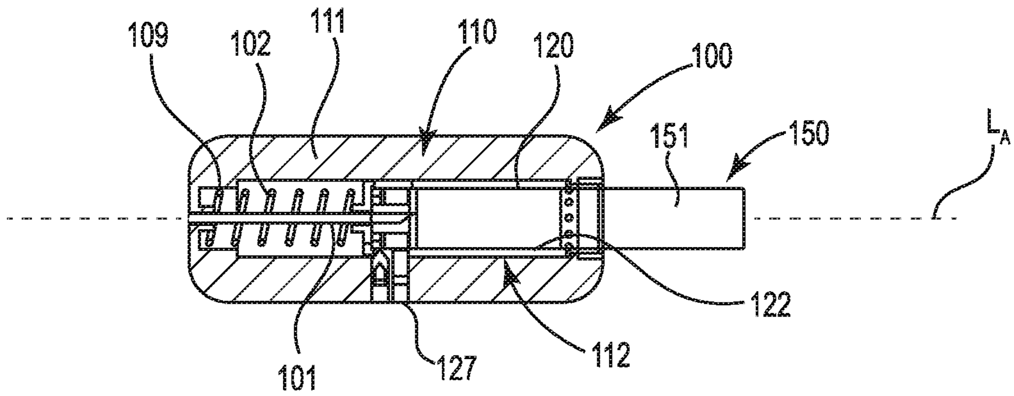
FIG. 4 is a cross-sectional schematic diagram of an illustrative inhaler system of FIG. 3.
Figure 5:
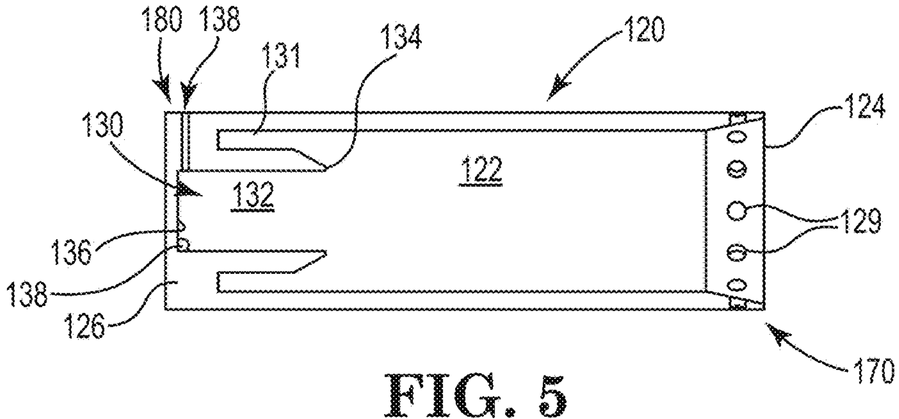
FIG. 5 is a cross-sectional schematic diagram of an illustrative sleeve.

FIG. 3 is a perspective view of an illustrative inhaler system 100. FIG. 4 is a cross-sectional schematic diagram of an illustrative inhaler system 100 of FIG. 3. FIG. 5 is a cross-sectional schematic diagram of an illustrative sleeve 120 of the inhaler system 100.

The inhaler system 100 includes an inhaler article 150 and a separate holder 110. The inhaler article 150 may be received within the holder 110 to activate or pierce a capsule 160 disposed within the inhaler article 150. The inhaler article 150 remains in the holder 110 during use by the consumer. The holder 110 is configured to induce swirling inhalation airflow entering the received inhaler article 150. The holder 110 is configured to breach or open the deformable element 158 of the inhaler article 150.

The inhaler system 100 includes the inhaler article 150 and the holder 110. The inhaler article 150 includes the body 151 that extends along an inhaler longitudinal axis LA. The holder 110 includes a movable sleeve 120 that retains the inhaler article 150 received in the sleeve cavity 122.

The holder 110 for the inhaler article 150 includes a housing 111 comprising a housing cavity 112 for receiving the inhaler article 150 and the sleeve 120 configured to retain the inhaler article 150 within the housing cavity 112. The sleeve 120 defines a sleeve cavity 122 and is movable within the housing cavity 112 along the longitudinal axis LA of the housing 111. The sleeve 120 comprises a first open end 124 and a second opposing end 126. The second opposing end 126 of the sleeve 120 is configured to allow air to enter the sleeve cavity 122. The second opposing end 126 of the sleeve 120 is configured to induce a swirl on the air entering the sleeve cavity 122.

The holder 110 may include a piercing element 101 fixed to and extending from a housing inner surface 109. The piercing element 101 may be configured to extend through the second opposing end 126 of the sleeve 120 and into the sleeve cavity 122 along a longitudinal axis of the housing 111. The holder 110 may include a spring element 102 configured to bias the sleeve 120 away from the piercing element 101.

The sleeve 120 may include an elongated slot extending along a longitudinal length of the sleeve 120. The housing 111 may further comprises a pin 127 extending from an inner surface 109 of the housing cavity 112. The pin 127 may be configured to mate with the elongated slot.

FIG. 5 is a cross-sectional schematic diagram of an illustrative sleeve 120. The second opposing end 126 of the sleeve 120 comprises a sleeve tubular element 130 defining a central passage 132, an end surface 136 and an open end 134. The central passage 132 in fluid communication with the sleeve cavity 122. The sleeve tubular element 130 open end 132 may extend into the sleeve cavity 122. The sleeve tubular element 130 includes at least one air inlet 138 allowing air to enter into the central passage 132. The at least one air inlet 138 extends in a direction that is tangential to the central passage 132.

Figure 6:
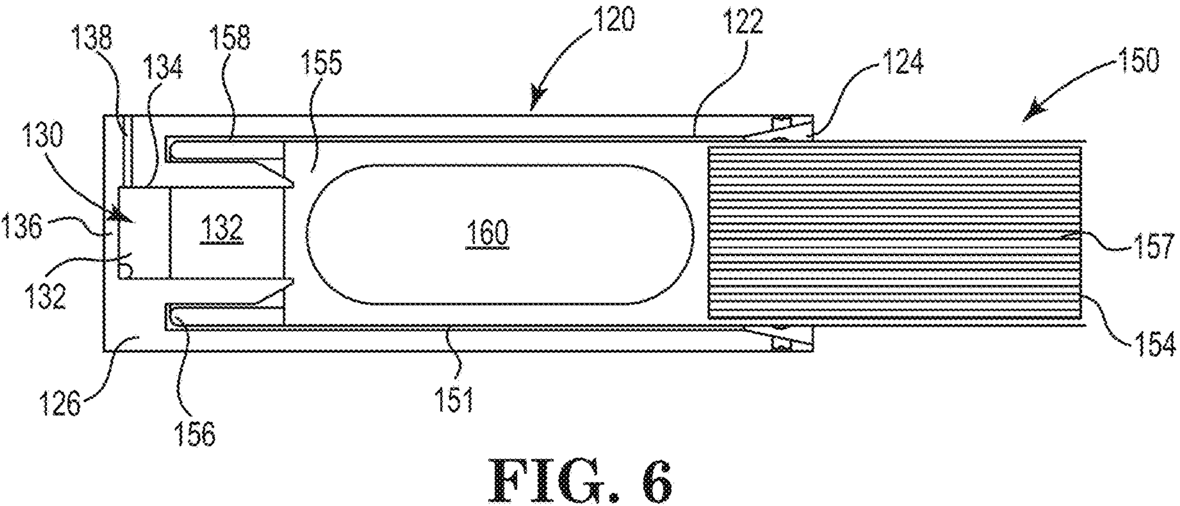
FIG. 6 is a cross-sectional schematic diagram of the illustrative inhaler article of FIG. 1 received in the sleeve illustrated in FIG. 5.

The distal end 156 of the inhaler article 150 may slide onto the sleeve tubular element 130 as illustrated in FIG. 6. The sleeve tubular element 130 open end 134 changes the deformable element 158 from a closed configuration to an open configuration allowing swirling or rotating inhalation air to flow directly into the inhaler article 150 capsule cavity 155.

Upon insertion of the inhaler article 150 into the holder 110, the sleeve tubular element 130 open end 134 deforms and urges through the deformable element 158 so that the sleeve tubular element 130 extends into the received inhaler article 150 tubular element 153. The deformable element 158 may be biased towards the longitudinal axis of the inhaler article in the open configuration so that the inhaler article 150 grips onto the holder, thus holding the inhaler article 150 in place in the holder 110.

Inhalation air inlets 138 enter the sleeve tubular element 130 at a tangent to the central passage 132 and form swirling inhalation airflow to the capsule cavity 155 of a received inhaler article 150. The swirling inhalation airflow flows along the capsule cavity 155 of a received to induce capsule rotation and release particles into the inhalation airflow.

The sleeve tubular element 130 may extend into the sleeve cavity 122 and forms an annular recess 131 with the sleeve cavity 122 configured to receive a distal end 156 of an inhaler article 150. The projection formed by the sleeve tubular element 130 slides into the inhaler article 150 capsule cavity 155. The sleeve tubular element 130 is configured here to extend into a distal end 156 of an inhaler article 150 received within the sleeve cavity 122.

The sleeve tubular element 130 may extend into the sleeve cavity 122 about 5 mm and have an outer diameter of about 6.5 mm and an inner diameter of about 4 mm. The central capsule cavity 155 of a received inhaler article 150 may have an inner diameter of about 6.6 mm to provide an interference fit with the sleeve tubular element 130 and annular recess 131.

The sleeve 120 defines a first air inlet zone 170 comprising at least one air aperture 129 through the sleeve 120. The first air inlet zone 170 proximate to the first open end 124 of the sleeve 120. The first air inlet zone 170 is configured to allow air to flow to an airflow channel formed between the sleeve 120 and the housing 111. The sleeve comprises a second air inlet zone 180 in downstream from the first air inlet zone 170. The second air inlet zone 180 comprising the second opposing end 126 of the sleeve 120 configured to allow air to enter the sleeve cavity 122. The second air inlet zone 180 comprising at least one air aperture or air inlet 138 through the sleeve 120 and into the sleeve tubular element 130 having a central passage 132.

FIG. 6 is a cross-sectional schematic diagram of an illustrative inhaler article 150 of received in the sleeve 120 illustrated in FIG. 5. As illustrated in FIG. 6, the capsule cavity 155 of the inhaler article 150 aligns and mates with and extends into the central passage 132 of the sleeve tubular element 130. The sleeve tubular element 130 forms the upstream end of the capsule cavity 155. The deformable element 158 is opened up back on to the capsule cavity 155 sidewall and providing an interference fit within the annular recess 131.

The invention claimed is:

1. An inhaler system comprising: an inhaler article for use in the inhaler system for providing a dry powder to lungs of a user, the inhaler article comprising:

a body extending along a longitudinal axis from a mouthpiece end to a distal end;

a capsule cavity defined within the body and bounded downstream by a filter element and bounded upstream and distally by a deformable element, the deformable element deforms by folding back onto itself to define an open aperture and to form an open distal end and allow the inhaler article to receive swirling or rotational inhalation airflow during consumption through the open distal end; and a capsule disposed within the capsule cavity and containing the dry powder; and a holder for the inhaler article, wherein the holder is configured to provide swirling or rotational inhalation airflow to the inhaler article, wherein the holder comprises a sleeve configured to retain the inhaler article within a housing cavity, the sleeve comprising a sleeve cavity and being movable within the housing cavity along a longitudinal axis of the housing cavity, wherein the sleeve comprises a first open end and a second opposing end, wherein the second opposing end of the sleeve is configured to allow air to enter the sleeve cavity; and the second opposing end of the sleeve comprises a sleeve tubular element extending into the sleeve cavity, the sleeve tubular element is configured to extend through the deformable element of the inhaler article and secure the inhaler article within the sleeve.

2. The inhaler system according to claim 1, wherein the sleeve tubular element forms an upstream boundary of the capsule cavity.

3. The inhaler system according to claim 1, wherein the sleeve tubular element folds the deformable element back onto itself to define the open aperture.

4. The inhaler system according to claim 3, wherein at least a portion of the deformable element is formed of paper.

5. The inhaler system according to claim 3, wherein the open aperture is configured to receive the swirling airflow from the sleeve tubular element.

* * * * *